United States Patent [19]

Eckstein et al.

[11] 4,184,977
[45] Jan. 22, 1980

[54] FLUORESCENT DYESTUFFS

[75] Inventors: Udo Eckstein, Cologne; Hans Theidel, Leverkusen, both of Fed. Rep. of Germany

[73] Assignee: Bayer Aktiengesellschaft, Leverkusen, Fed. Rep. of Germany

[21] Appl. No.: 922,186

[22] Filed: Jul. 5, 1978

[30] Foreign Application Priority Data

Jul. 7, 1977 [DE] Fed. Rep. of Germany ....... 2730644

[51] Int. Cl.² ................. C07D 403/00; C07D 413/00
[52] U.S. Cl. ................. 252/301.22; 252/301.24; 252/301.25; 252/301.26; 542/454; 542/456; 542/458; 542/459; 542/464; 542/467
[58] Field of Search ............. 542/454, 456, 458, 459, 542/464, 467; 252/301.22, 301.25, 301.26, 301.24

[56] References Cited

U.S. PATENT DOCUMENTS

| | | | |
|---|---|---|---|
| 3,684,729 | 8/1972 | Tuite | 542/454 X |
| 3,697,513 | 10/1972 | Siegrist | 252/301.22 X |
| 3,725,395 | 4/1973 | Siegrist et al. | 542/459 |
| 3,872,114 | 3/1975 | Sahm | 542/454 |
| 4,066,830 | 1/1978 | Kormany et al. | 542/456 |

FOREIGN PATENT DOCUMENTS 7016013 5/1971 Netherlands ............... 542/456

OTHER PUBLICATIONS

Manecke et al., "3,4-Diaminostyrene," in Chem. Abs. 60236t, Mar. 25, 1974, vol. 80.
Ciba, "Bisoxazoles," in Chem. Abs., vol. 63, 1965, 13460.

*Primary Examiner*—Arthur P. Demers
*Attorney, Agent, or Firm*—Sprung, Felfe, Horn, Lynch & Kramer

[57] ABSTRACT

Fluorescent dyestuffs of the formula

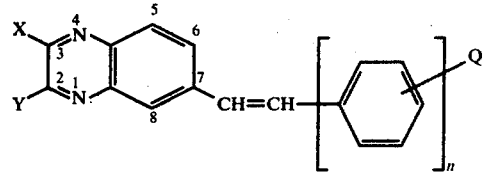

wherein

X and Y denote hydrogen, halogen, alkyl, aralkyl, alkenyl, hydroxyl, amino, alkoxy, aralkoxy, cycloalkoxy, aryloxy, alkylmercapto, alkylamino, dialkylamino, morpholino, piperidino, piperazino, pyrrolidino, acylamino or arylamino.

Q denotes hydrogen, pyrazol-1-yl, oxazol-2-yl, benzoxazol-2-yl, naphthoxazol-2-yl, 1,2,4-oxadiazol-5-yl, 1,3,4-oxadiazol-2-yl, isoxazol-3-yl, isoxazol-5-yl, thiazol-2-yl, benzthiazol-2-yl, 1,3,4-thiadiazol-2-yl, imidazol-2-yl, benzimidazol-2-yl, 1,2,3-triazol-2-yl, 1,2,3-triazol-4-yl, 1,2,4-triazol-3-yl, 1,2,4-triazol-5-yl, 1,3,5-triazin-2-yl, 2H-benzotriazol-2-yl, 2H-naphthotriazol-2-yl, 1,2,3,4-tetrazol-5-yl, 1,2,3,4-tetrazol-1-yl, benzo[b]-furan-2-yl, naphtho[2,1-b]-furan-2-yl, benzo[b]-thiophen-2-yl, naphtho[2,1-b]-thiophen-2-yl, pyrimidin-2-yl, pyridin-2-yl, quinazolin-4-yl or quinazolin-2-yl, and, if n=0, also naphthyl, stilben-4-yl, benzo[b]-furan-6-yl, dibenzofuran-3-yl, dibenzofuran-2-yl, quinoxalin-5-yl, quinazolin-6-yl or 2H-benzotriazol-5-yl and n denotes 0, 1 or 2, it being possible for the substituents X, Y and Q and the remaining cyclic radicals to be further substituted by non-chromophoric substituents which are customary for whiteners, are suitable for whitening the most diverse synthetic, semi-synthetic and natural organic high-molecular materials.

3 Claims, No Drawings

FLUORESCENT DYESTUFFS

The invention relates to fluorescent dyestuffs, processes for their preparation and their use for whitening organic materials.

The new compounds to the formula

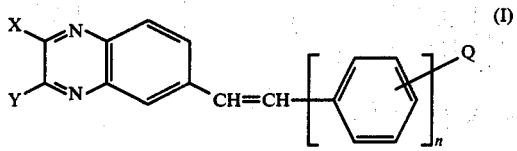

wherein
X and Y denote hydrogen, halogen, alkyl, aralkyl, alkenyl, hydroxyl, amino, alkoxy, aralkoxy, cycloalkoxy, aryloxy, alkylmercapto, alkylamino, dialkylamino, morpholino, piperidino, piperazino, pyrrolidino, acylamino or arylamino, Q denotes hydrogen, pyrazol-1-yl, oxazol-2-yl, benzoxazol-2-yl, naphthoxazol-2-yl, 1,2,4-oxadiazol-5-yl, 1,3,4-oxadiazol-2-yl, isoxazol-3-yl, isoxazol-5-yl, thiazol-2-yl, benzthiazol-2-yl, 1,3,4-thiadiazol-2-yl, imidazol-2-yl, benzimidazol-2-yl, 1,2,3-triazol-2-yl, 1,2,3-triazol-4-yl, 1,2,4-triazol-3-yl, 1,2,4-triazol-5-yl, 1,3,5-triazin-2-yl, 2H-benzotriazol-2-yl, 2H-naphthotriazol-2-yl, 1,2,3,4-tetrazol-5-yl, 1,2,3,4-tetrazol-1-yl, benzo[b]-furan-2-yl, naphtho[2,1-b]-furan-2-yl, benzo[b]-thiophen-2-yl, naphtho[2,1-b]-thiophen-2-yl, pyrimidin-2-yl, pyrimidin-2-yl, pyridin-2-yl, quinazolin-4-yl or quinazolin-2-yl, and, if n=0, also naphthyl, stilben-4-yl, benzo[b]-furan-6-yl, dibenzofuran-3-yl, dibenzofuran-2-yl, quinoxalin-5-yl, quinazolin-6-yl or 2H-benzotriazol-5-yl, and n denotes 0, 1 or 2, it being possible for the substituents X, Y and Q and the remaining cyclic radicals to be further substituted by non-chromophoric substituents which are customary for whiteners. n is preferably 0 or 1.

Examples of non-chromophoric substituents are halogen, optionally substituted alkyl, optionally substituted alkenyl, aryl, aralkyl, optionally substituted alkoxy, alkoxycarbonyl, optionally substituted aminocarbonyl, cyano, alkylsulphonyl, alkoxysulphonyl, optionally substituted aminosulphonyl, acyl, acylamino, hydroxyl, aryloxy, aralkoxy, alkenyloxy,, aryloxycarbonyl, aralkoxycarbonyl, carboxyl or acyloxy.

Alkyl is, in particular, $C_1-C_4$-alkyl, which can be monosubstituted by hydroxyl, $C_1-C_4$-alkoxy, cyano, carboxyl, $C_1-C_4$-alkoxycarbonyl, aminocarbonyl, chlorine or bromine, or trifluoromethyl.

Alkenyl is, in particular, $C_2-C_5$-alkenyl, which can be monosubstituted by hydroxyl, $C_1-C_4$-alkoxy, cyano, carboxyl, $C_1-C_4$-alkoxycarbonyl, chlorine or bromine.

Halogen is, in particular, fluorine, chlorine and bromine, preferably chlorine. Aryl is, in particular, phenyl which is optionally substituted by $C_1-C_4$-alkyl, trifluoromethyl, chlorine, bromine, carboxyl, cyano, $C_1-C_4$-alkoxycarbonyl or $C_1-C_4$-alkoxy.

Aralkyl is, in particular, phenyl $C_1-C_4$-alkyl, which can also be substituted in the phenyl nucleus by chlorine, methyl or methoxy.

Alkoxy is, in particular, $C_1-C_4$-alkoxy or a radical of the formula

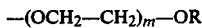

wherein
R denotes hydrogen or $C_1-C_4$-alkyl and
m denotes an integer from 1 to 20.

Cycloalkoxy is, in particular, cyclopentyloxy and cyclohexyloxy.

Acyl is, in particular, $C_1-C_4$-alkylcarbonyl, $C_1-C_4$-alkylsulphonyl, benzoyl which is optionally substituted by methyl, methoxy or chorine or benzenesulphonyl which is optionally substituted by methyl, methoxy or chlorine.

Possible substituents of the amonocarbonyl and aminosulphonyl radicals are, in particular, $C_1-C_4$-alkyl, phenyl which is optionally substituted by methyl, methoxy or chlorine or phenyl-$C_1-C_4$-alkyl.

Preferred compounds correspond to the formula

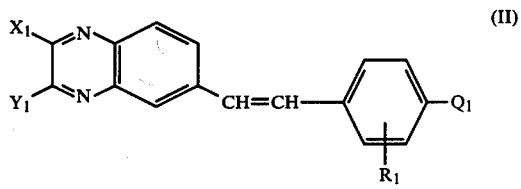

wherein
$X_1$ and $Y_1$ denote hydrogen, chlorine, $C_1-C_4$-alkylamino, di-$C_1-C_4$-alkylamino, morpholino, piperidino, phenylamino which is optionally substituted by methyl, methoxy or chlorine or a radical of the formula

$R_1$ denotes hydrogen, chlorine, $C_1-C_4$-alkyl, $C_1-C_4$-alkoxy, $C_1-C_4$-alkoxycarbonyl or cyano,
$R_2$ denotes hydrogen, $C_1-C_4$-alkyl, benzyl or phenyl,
q denotes an integer from 0 to 7 and
$Q_1$ denotes chlorine, bromine, cyano, carboxyl, $C_1-C_4$alkoxycarbonyl or a radical of the formula

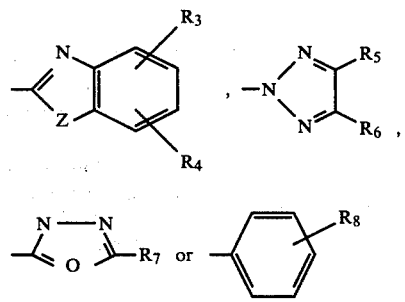

$R_3$ denotes hydrogen, chlorine, $C_1-C_4$-alkyl, phenyl $C_1-C_3$-alkyl, cyclohexyl, phenyl, $C_1-C_4$-alkoxy, $C_1-C_4$-alkylsulphonyl, $C_1-C_4$-alkoxycarbonyl, cyano or carboxyl or, together with $R_4$, a fused-on 1-cyclopenteno, 1-cyclohexeno or benzo ring which is optionally substituted by 1 to 4 methyl groups, $R_4$ denotes hydrogen, chlorine or methyl or, together with $R_3$, a fused-on 1-cyclopenteno, 1-cyclohexeno or benzo ring which is optionally substituted by 1 to 4 methyl groups, $R_5$ denotes $C_1-C_4$-alkyl, phenyl or styryl or, together with $R_6$, a fused-on benzo ring which is optionally substituted by $C_1$-$C_4$-alkyl, $C_1$-$C_4$-alkoxy or chlorine or fused-on naphtho, $R_6$ denotes hydrogen, $C_1$-$C_4$-alkyl or phenyl or, together with $R_5$, a fused-on benzo ring which is optionally substituted by $C_1$-$C_4$-alkyl, $C_1$-$C_4$-alkoxy or chlorine or fused-on naphtho, $R_7$ denotes phenyl, styryl, biphenylyl or naphthyl, optionally substituted by $C_1$-$C_4$-alkyl, $C_1$-$C_4$-alkoxy, $C_1$-$C_4$-alkoxycarbonyl, cyano or chlorine, $R_8$ denotes hydrogen, $C_1$-$C_4$-alkyl, $C_1$-$C_4$-alkoxy, $C_1$-$C_4$-alkoxycarbonyl, cyano or a benzoxazol-2-yl radical which is optionally substituted by $C_1$-$C_4$-alkoxycarbonyl, cyano or chlorine, Z denotes O, S or $NR_9$ and $R_9$ denotes hydrogen, $C_1$-$C_4$-alkyl, acetyl, benzoyl, benzyl or phenyl. Particularly valuable compounds correspond to the formula

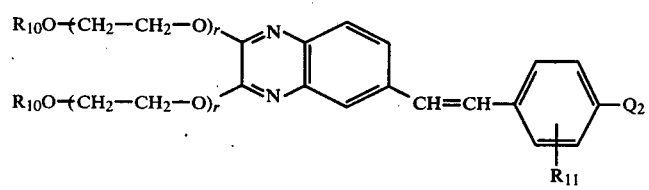

wherein $R_{10}$ denotes $C_1$-$C_4$-alkyl,
$R_{11}$ denotes hydrogen or cyano,
r denotes an integer from 0 to 2,
$Q_2$ denotes as radical of the formulae

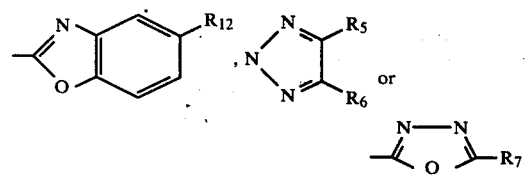

$R_{12}$ denotes hydrogen, chlorine, $C_1$-$C_4$-alkyl, phenyl $C_1$-$C_3$-alkyl, cyclohexyl, phenyl, $C_1$-$C_4$-alkoxy, $C_1$-$C_4$-alkylsulphonyl, $C_1$-$C_4$-alkoxycarbonyl, cyano or carboxyl and $R_5$, $R_6$ and $R_7$ have the abovementioned meaning.

The fluorescent dyestuffs according to the invention can be prepared by various routes. Preferably,
(a) a phosphono compound of the formula

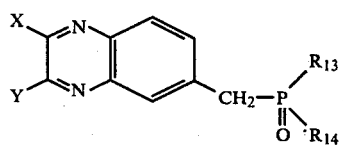

wherein

X and Y have the abovementioned meaning and the benzene ring can contain further non-chromophoric substituents and $R_{13}$ and $R_{14}$ denote $C_1$-$C_{14}$-alkoxy, $C_5$-$C_6$-cycloalkoxy, phenoxy or phenyl, is subjected to a condensation reaction with an aldehyde of the formula

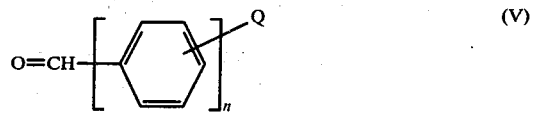

wherein

Q and n have the abovementioned meaning and the benzene ring can contain further non-chromophoric substituents, or (b) a phosphono compound of the formula

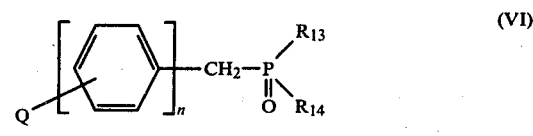

wherein

Q, $R_{13}$, $R_{14}$ and n have the abovementioned meaning and the benzene ring can be substituted by non-chromophoric substituents, is subjected to a condensation reaction with an aldehyde of the formula

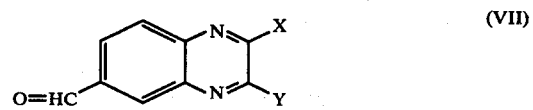

wherein

X and Y have the abovementioned meaning and the benzene ring can be substituted by non-chromophoric substituents, in organic solvents in the presence of basic condensing agents.

The solvents advantageously chosen are inert solvents, for example hydrocarbons, such as toluene or xylene, or alcohols, such as methanol, ethanol, isopropanol, butanol, glycol, glycol ethers, such as 2-methoxyethanol; hexanol, cyclohexanol or cyclooctanol, and also ethers, such as diisopropyl ether, dioxane or tetrahydrofurane, and furthermore formamides or N-methylpyrrolidone. Dipolar organic solvents, such as dimethylformamide and dimethylsulphoxide, are particularly suitable.

Possible condensing agents are strongly basic compounds, such as alkali metal hydroxides or alkaline earth metal hydroxides, alkali metal amides or alkaline earth metal amides and alkali metal alcoholates or alkaline earth metal alcoholates, for example potassium hydroxide, sodium hydroxide, potassium tert.-butylate, sodium amide or sodium methylate, and also the alkali metal compounds of dimethylsulphoxide, and alkali metal hydrides, as well as alkali metal dispersions in some cases.

The reaction is preferably carried out in the temperature range from 0° to 100° C.

The compounds according to the invention are also obtained when (c) instead of the phosphono compounds (IV) and (VI), the corresponding quaternary phosphonium salts, for example the triphenylphosphonium salts, are employed and these are subjected to a condensation reaction with the aldehydes (V) and (VII) in accordance with a Wittig reaction via the phosphorylenes stage or (d) the corresponding aldehyde-anils are reacted with the 6-methylquinoxalines in dimethylformamide in accordance with a Siegrist reaction in the presence of basic condensing agents.

Further conversions which are in themselves known, such as halogenations, functional modifications of carboxyl groups, introduction of chloromethyl groups or replacement of halogen atoms by cyano groups, can also be carried out on the reaction products of the above processes.

Because of thier absorption in the ultraviolet region and their fluorescene, the compounds according to the invention are suitable for whitening the most diverse synthetic, semi-synthetic and natural organic high-molecular materials, such as are given in detail in the following text.

I.

Synthetic organic high-molecular materials:

(a) Polymerisation products based on organic compounds containing at least one polymerisable carbon-carbon double bond, that is to say their homopolymers or copolymers as well as their after-treatment products, such as, for example, cross-linking, grafting or degradation products, polymer blends and the like, of which the following may be mentioned as examples: polymers based on $\alpha,\beta$-unsaturated carboxylic acids, especially on acrylic compounds (such as, for example, acrylic esters, acrylic acids, acrylonitrile, acrylamides and their derivatives or their methacrylic analogues) and on olefine hydrocarbons (such as, for example, ethylene, propylene, isobutylene, styrenes and dienes, such as, in particular, butadiene and isoprene, that is to say, also rubbers and rubber-like polymers, and also so-called ABS polymers), polymers based on vinyl and vinylidene compounds (such as, for example, vinyl esters, vinyl chloride, vinylsulphonic acid, vinyl ether, vinyl alcohol, vinylidene chloride and vinylcarbazole), on halogenated hydrocarbons (chloroprene and post-halogenated ethylenes), on unsaturated aldehydes and ketones (for example acrolein and the like) and on allyl compounds and the like, graft polymerisation products (for example those obtained by the grafting on of vinyl monomers), crosslinking products (for example those obtained by means of bifunctional or polyfunctional crosslinking agents, such as divinylbenzene, polyfunctional allyl compounds or bisacrylic compounds) or are obtainable by partial degradation (hydrolysis or depolymerisation) or modification of reactive groupings (for example esterification, etherification, halogenation or spontaneous crosslinking).

(b) Other polymerisation products, such as are obtainable, for example, by ring opening, for example polyamides of the polycaprolactam type, and also formaldehyde polymers or polymers which are obtainable either via polyaddition or via polycondensation, such as polyethers, polythioethers, polyacetals or thioplasts.

(c) Polycondensation products or precondensates based on bifunctional or polyfunctional compounds having condensable groups, their homocondensation and co-condensation products as well as after-treatment products, of which the following may be mentioned as examples: polyesters, that is to say polyesters which are saturated (for example polyethylene terephthalate) or unsaturated (for example maleic acid/dialcohol polycondensates as well as their crosslinking products with copolymerisable vinyl monomers), unbranched or branched (also those based on polyhydric alcohols, such as, for example, alkyd resins); and polyamides (for example hexamethylenediamine adipate), maleate resins, melamine resins, phenolic resins, aniline resins, furane resins, carbamide resins and also their precondensates and products of analogous structure, polycarbonates, silicone resins and others.

(d) Polyaddition products, such a polyurethanes (crosslinked and non-crosslinked) and epoxide resins.

II.

Semi-synthetic organic materials, such as, for example, cellulose esters or mixed esters (acetate and propionate), nitrocellulose, cellulose ethers and regenerated cellulose (viscose and copper ammonium cellulose), or their after-treatment products, and casein plastics.

III.

Natural organic materials of animal or vegetable origin, for example those based on cellulose or proteins, such as wool, cotton, silk, bast, jute, hemp, skins and hairs, leather, finely divided wood compositions and natural resins (such as colophonium and, in particular, lacquer resins), and also rubber, guttapercha and balata, as well as their after-treatment and modification products (for example those obtained by curing, crosslinking or grafting), degradation products (for example those obtained by hydrolysis or depolymerisation) and those products obtainable by modifying reactive groups (for example by acylation, halogenation, crosslinking and the like).

The organic materials which can be used can be in the most diverse states of processing (raw materials, semi-finished goods or finished goods) and states of aggregation. On the one hand, they can be in the form of structures of the most diverse shapes, that is to say, for example, predominantly three-dimensional bodies, such as blocks, slabs, profiles, tubes, injection mouldings or the most diverse machined articles, chips or granules or foams; predominantly two-dimensional bodies, such as films, sheets, lacquers, tapes, coverings, impregnations and coatings, or predominantly one-dimensional bodies, such as filaments, fibres, flocks, bristles and wires. The said materials can, on the other hand, also be in unshaped states in the most diverse homogeneous and inhomogeneous forms of division and states of aggregation, for example in the form of powders, solutions, emulsions, dispersions and latices (examples: lacquer solutions, polymer dispersions, sols, jellies, putties, pastes, waxes, adhesive compositions and trowelling compounds, and the like).

Fibre materials can be, for example, in the form of continuous filaments, stape fibres, flocks, hanks, textile filaments, yarns, threads, fibre fleeces, felts, waddings, flocked structures or woven textile fabrics or textile laminates, knitted fabrics and papers, cardboards or paper pulps and the like.

The compounds to be used according to the invention are also of importance for the treatment of organic textile materials, especially woven textile fabrics. Where fibres, which can be in the form of staple fibres or continuous filaments or in the form of hanks, woven fabrics, knitted fabrics, fleeces, flocked substrates or laminates, are to be whitened according to the invention, this is advantageously effected in an aqueous medium, in which the compounds concerned are present in a finely divided form (suspensions or, in some cases, solutions). If appropriate, dispersing agents can be added during the treatment, such as, for example, soaps, polyglycol ethers of fatty alcohols, fatty amines or alkylphenols, cellulose sulphite waste liquors or condensation products of optionally alkylated naphthalenesulphonic acids and formaldehyde. It proves particularly appropriate to carry out the treatment in a neutral, weakly alkaline or acid bath. It is also advantageous if the treatment is effected at elevated temperatures of about 50° to 100° C., for example at the boiling point of the bath or near it (about 90° C.). Solutions in organic solvents can also be used for the finishing according to the invention, as is practiced in the dyeing trade in so-called solvent dyeing (pad-thermofix application or the exhaustion dyeing process in drum dyeing machines), for example for polyamide and polyester substrates.

The new whiteners to be used according to the invention can also be added to, or incorporated in, the materials before or during their shaping. Thus, for example, they can be added to the compression moulding composition or injection moulding composition in the production of films, sheets, tapes or shaped articles, or they can be dissolved or dispersed, or otherwise homogeneously finely distributed, in the spinning composition before spinning. The whiteners can also be added to the starting substances, reaction mixtures or intermediate products for the preparation of fully synthetic or semi-synthetic organic materials, that is to say also before or during the chemical reaction, for example in the case of a polycondensation reaction (that is to say also to the precondensates), or in the case of a polymerisation reaction (that is to say also to the prepolymers) or a polyaddition reaction.

The new whiteners can, of course, also be employed in all cases where organic materials for the type indicated above are combined with inorganic materials in any form (typical examples: washing agents or white pigments in organic substances).

The new whitening substances are distinguished by a particularly good resistance to heat, fastness to light and resistance to migration.

The amount of the new whiteners to be used according to the invention, relative to the material to be whitened, can vary within wide limits. In certain cases, a distinct and durable effect is achieved even with very small amounts, for example 0.001% by weight. However, amounts of up to about 0.5% by weight and more can be used. For most practical purposes, amounts between 0.01 and 0.2% by weight are of preferred interest.

The new compounds, which are used as whiteners, can also be employed, for example, as follows:

(a) Mixed with dyestuffs or pigments or as an additive to dyebaths, printing pastes, discharge pastes or reserve pastes. Furthermore, also, for the after-treatment of dyeings, prints or discharge prints.

(b) Mixed with so-called "carriers", antioxidants, light stabilisers, heat stabilisers and chemical bleaching agents or as an additive to bleaching baths.

(c) Mixed with crosslinking agents or finishing agents, such as starch or synthetically accessible finishes. The products according to the invention can also advantageously be added to the liquors used for achieving a creaseproof finish.

(d) In combination with washing agents. The washing agent and brightener can be added separately to the wash baths which are to be used. It is also advantageous to use washing agents which contain the whiteners as an admixture. Examples of suitable washing agents are soaps, salts of sulphonate washing agents, such as, for example, of sulphonated benzimidazoles which are substituted on the 2-carbon atom by higher alkyl radicals, and also salts of monocarboxylic acid esters of 4-sulphophthalic acid with higher fatty alcohols, and furthermore salts of fatty alcohol sulphonates, alkylarylsulphonic acids or condensation products of higher fatty acids with aliphatic hydroxysulphonic or aminosulphonic acids. Non-ionic washing agents can also be used, for example polyglycol ethers which are derived from ethylene oxide and higher fatty alcohols, alkylphenols or fatty amines.

(e) In combination with polymeric carriers (polymerisation, polycondensation or polyaddition products), in which the whiteners are incorporated, optionally in addition to other substances, in the dissolved or dispersed from, for example in the case of coating agents, impregnating agents or binding agents (solutions, dispersions and emulsions), textiles, fleeces, paper and leather.

(f) As additives to the most diverse industrial products, in order to render these more marketable or to avoid disadvantages in their usability, for example as an additive to sizes, adhesives, toothpastes, paints and the like.

(g) In combination with other substances having a whitening action (for example for the purpose of altering the shade).

(h) In spinning bath preparations, that is to say as additives to spinning baths, such as are used for improving the slip for the further processing of synthetic fibres.

The compounds of the formula initially indicated can be used as scintillators for various purposes of a photographic nature, such as for electrophotographic reproduction or for supersensitisation.

If the whitening process is combined with other treatment or finishing methods, the combined treatment is advantageously effected with the aid of corresponding stable formulations. Such formulations are characterised in that they contain the whitening compounds of the general formula initially indicated, as well as dispersing agents, washing agents, carriers, dyestuffs, pigments of finishing agents.

In the treatment of a range of fibre substrates, for example polyester fibres, with the whiteners according to the invention, the procedure followed is appropriately to impregnate these fibres with the aqueous dispersions of the whiteners at temperatures below 75° C., for example at room temperature, and to subject them to a dry heat treatment at temperatures above 100° C., it being generally advisable additionally to dry the fibre material beforehand at a moderately elevated temperature, for example at not less than 60° C. up to about 100° C. The heat treatment in the dry state is then advantageously carried out at temperatures between 120° and 225° C., for example by warming in a drying chamber, by ironing in the temperature range indicated or also by treatment with dry, superheated steam. The drying and dry heat treatment can also be carried out in immediate succession or be combined in a single operation.

EXAMPLE 1

12 g (0.22 mol) of sodium methylate are added in portions to a solution of 22.3 g (0.1 mol) of 2-(4-formyl-phenyl)-benzoxazole and 31.2 g (0.1 mol) of 2,3-dimethoxy-6-dimethoxyphosphonomethylquinoxaline in 300 ml of dimethylformamide in the course of 20 minutes. The reaction mixture is stirred at 50° C. in the course of 4 hours, then discharged onto 1 l of ice-water and adjusted to pH 4 to 5 with acetic acid. After cooling, the yellowish precipitate is filtered off, washed with water and methanol and dried. 28.5 g (70% of theory) of crude product of the formula of 20 minutes and the mixture is stirred at the reflux temperature for 4 hours. Thereafter, the succinimide is filtered off, the filter cake is rinsed with hot carbon tetrachloride and the filtrate is evaporated almost to dryness. The residue is filtered off and washed with petroleum ether (40° to 80° C.). 41.4 g (73% of theory) of the bromomethyl compound of melting point 149° C. are obtained.

70.6 g (0.25 mol) of crude 2,3-dimethoxy-6-bromomethylquinoxaline are warmed slowly to 140° C. with 185 g of trimethyl phosphite under a nitrogen atmosphere, whilst stirring, and the mixture is then stirred at this temperature for 4 hours. Most of the excess trimethyl phosphite is then distilled off in vacuo and 100 ml of cyclohexane are added to the residue. The mixture is cooled to 0° C. and the product is allowed to crystallise out. 66.5 g (86% of theory) of colourless crystals of melting point 114° C., which melt at 114° to 115° C.

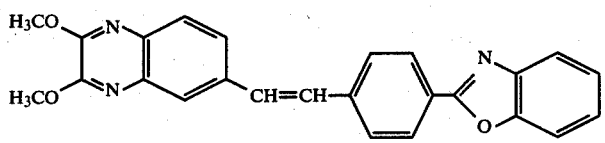

(1)

which is purified by recrystallising from xylene several times, are thus obtained. The substance exhibits reddish-tinged blue fluorescence when dissovled in dimethylformamide and has, when incorporated into polyethylene terephthalate, a powerful brightening effect with good fastness properties.

The dimethoxyphosphonomethyl compound of the formula

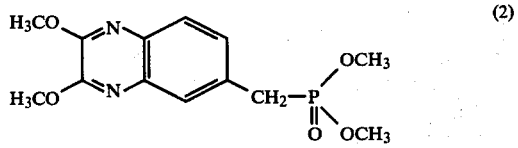

(2)

used is prepared in the following manner:

A solution of 1 ml of sodium methylate in 1 l of methanol is added dropwise to a suspension of 106.5 g (0.5 mol) of 2,3-dichloro-6-methylquinoxaline in 1 l of methanol at 20° to 30° C. in the course of one hour. The mixture is stirred at 40° C. for 5 hours and the solvent is distilled off in vacuo. 1 l of water is added to the residue and, after cooling, the solid is filtered off. 95.6 g (94% of theory) of colourless crystals of melting point 81° C., 81 to 82° C. when recrystallised from methanol, are obtained.

A mixture of 35.6 g (0.2 mol) of N-bromosuccinimide and 0.2 g of azoisobutyronitrile is added in portions to a solution of 40.8 g (0.2 mol) of 2,3-dimethoxy-6-methylquinoxaline and 0.2 g of dibenzoyl peroxide in 300 ml of anhydrous carbon tetrachloride at 60° C. in the course when recrystallised from methylcyclohexane, are obtained.

The phosphono compound of the formula

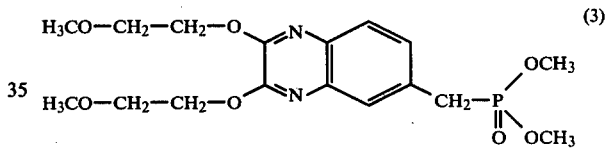

(3)

is prepared analogously.

2-(4-Formylphenyl)-benzoxazole was prepared in a known manner by brominating 2-tolylbenzoxazole and subsequently reacting the product with hexamethylenetetramine in acetic acid.

EXAMPLE 2

Analogously to Example 1, the reaction of (3) with 2-(4-formylphenyl)-benzoxazole gives 31.3 g (63% of theory) of the compound of the formula

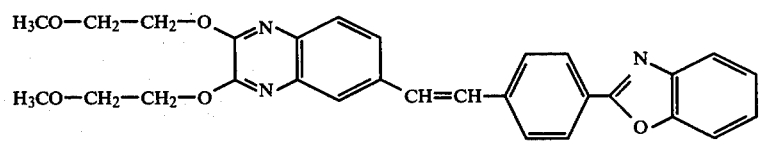

(4)

as yellow crystals. They can be purified by recrystallisation from toluene, bleaching earth being added; fluorescence in dimethylformamide: reddish-tinged blue.

EXAMPLE 3

In the same manner as in Example 1, 25.7 g (0.1 mol) of 5-chloro-2-(4-formylphenyl)-benzoxazole and 31.2 g (0.1 mol) of 2,3-dimethoxy-6-dimethoxyphosphonomethylquinoxaline give 33.9 g (76% of theory) of the compound of the formula

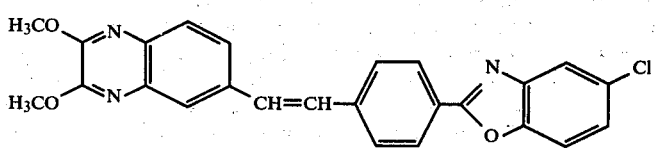

(5)

When the product is recrystallised from chlorobenzene, pale yellow crystals are obtained, the solution of which in dimethylformamide exhibits an intense reddish-tinged blue fluorescence.

EXAMPLE 4

24 g (0.44 mol) of sodium methylate are added in portions to a suspension of 38 g (0.2 mol) of 2,3-dihydroxy-6-formylquinoxaline (prepared from 2,3-dichloro-6-bromomethylquinoxaline and 5% strength nitric acid) and 63.5 g (0.2 mol) of 2-(4-dimethoxyphosphonomethylphenyl)-benzoxazole in 500 ml of dimethylformamide in the course of 30 minutes. The reaction mixture is stirred at 50° C. for 5 hours, discharged onto 1.5 l of ice-water and adjusted to pH 2 to 3 with concentrated hydrochloric acid. The yellowish precipitate is filtered off, washed with water and dried. 63 g (83% of theory) of the compound which, in one of the possible tautomeric forms, corresponds to the formula

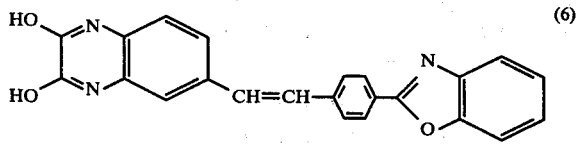

(6)

are obtained.

The compound is purified by recrystallisation from dimethylformamide.

The crude product of the formula (6) is boiled under reflux with five times the amount of thionyl chloride and catalytic amounts of dimethylformamide for 4 hours, after which the excess thionyl chloride is distilled off in vacuo. The residue is washed with ice-water and filtered off. 62.3 g (75% of theory) of the compound of the formula

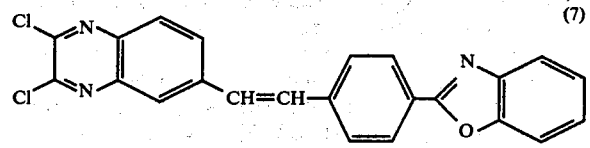

(7)

are obtained.

41.8 g (0.1 mol) of the crude product of the formula (7) are suspended in 200 ml of dioxane with 10.5 g (0.1 mol) of triethylamine, and 8.6 g (0.1 mol) of morpholine are added dropwise at room temperature. The mixture is stirred at 50° C. for 2 hours and then discharged onto 500 ml of water and the precipitate is filtered off. 38.5 g (82% of theory) of pale yellow crystals of the compound of the formula

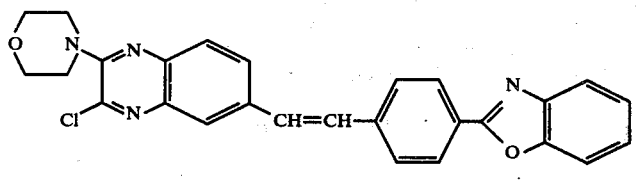

(8)

which is purified by recrystallisation from chlorobenzene are obtained.

18 g of 30% strength sodium methylate solution are added dropwise to a solution of 46.9 g (0.1 mol) of the compound of the formula (8) in 200 ml of dimethylformamide and the mixture is stirred at 30° to 40° C. for 3 hours. Thereafter, the reaction mixture is discharged onto 500 ml of water. The precipitate is filtered off, washed with water and dried. 40 g (86% of theory) of a light yellow crystalline powder of the compound of the formula

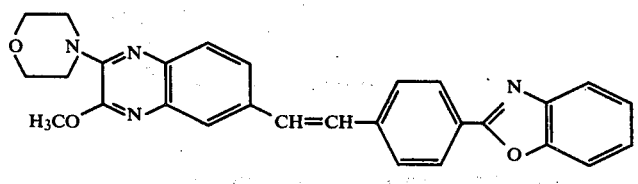

(9)

which is recrystallised from xylene, are obtained. The compound exhibits a neutral blue fluorescence in dimethylformamide.

EXAMPLE 5

In an analogous manner, the compound of the formula (7) gives, by reaction with (a) aniline and (b) sodium ethylate, the compound of the formula

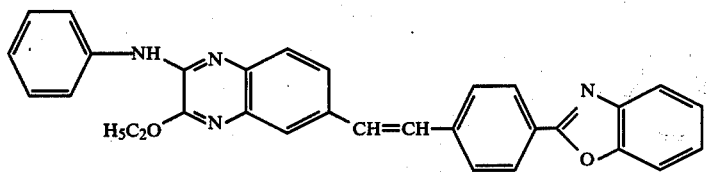

in the form of yellow crystals, which are recrystallised from chlorobenzene and exhibit an intense blue fluorescence in dimethylformamide.

Further particularly valuable compounds prepared

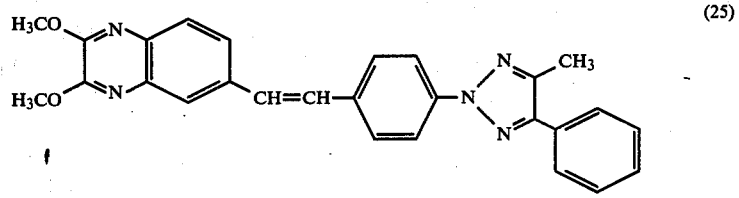

according to the invention, which correspond to the formula

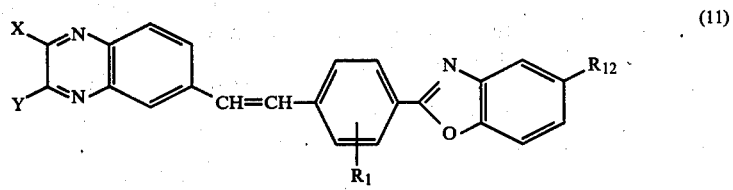

are listed in Table I which follows.

with acetic acid. After cooling to 0° C., the light yellow precipitate is filtered off, washed with methanol, dried and recrystallised from xylene. 28.5 g (63% of theory) of the compound of the formula which exhibits blue fluorescence when dissolved in dimethylformamide, are obtained.

Table I

| Compound | X | Y | $R_1$ | $R_{12}$ | Colour of fluorescence in dimethylformamide |
|---|---|---|---|---|---|
| 12 | Ethoxy | Ethoxy | H | H | reddish-tinged blue |
| 13 | Isopropoxy | Isopropoxy | 2-Chloro | H | reddish-tinged blue |
| 14 | Butoxy | Butoxy | 2-Ethoxycarbonyl | H | red-violet |
| 15 | $(OC_2H_4)_2—OCH_3$ | $(OC_2H_4)_2—OCH_3$ | H | tert.-Butyl | greenish-tinged blue |
| 16 | Methylamino | Methoxy | H | Methoxy | blue |
| 17 | N-Morpholino | Ethoxy | 2-Methoxy | H | blue |
| 18 | Diethylamino | Isopropoxy | 2-Methoxycarbonyl | H | blue |
| 19 | N-Morpholino | N-Morpholino | H | Carboxyl | deep blue |
| 20 | Anilino | Chloro | H | Cyano | blue |
| 21 | Diethylamino | Methoxy | 2-Cyano | H | blue |
| 22 | Anilino | Anilino | H | Methyl | greenish-tinged blue |
| 23 | Piperidino | Butoxyethoxy | 3-Chloro | Cyclohexyl | reddish-tinged blue |
| 24 | Benzoxy | Benzoxy | H | Benzyl | blue |

EXAMPLE 6

31.1 g (0.11 mol) of 2,3-dimethoxy-6-bromomethyl-quinoxaline, 56 g of triethyl phosphite and 100 ml of dimethylformamide are heated to 120° to 150° C. for 4 hours. Thereafter, the excess triethyl phosphite and most of the dimethylformamide are distilled off in vacuo. The residue and 26.3 g (0.1 mol) of 2-(4-formyl-phenyl)-4-methyl-5-phenyl-2H-1,2,3-triazole are dissolved in 250 ml of dimethylformamide, and 39.6 g of 30% strength sodium methylate solution are added dropwise. The mixture is stirred at 50° C. for 3 hours, diluted with 250 ml of methanol and adjusted to pH 7

EXAMPLE 7

24.6 g (0.1 mol) of 2,3-diethoxy-6-formylquinoxaline and 37.1 g (0.1 mol) of 2-(4-diethoxyphosphonomethyl-phenyl)-4-phenyl-2H-1,2,3-triazole are stirred in 250 ml of dimethylformamide, and 36 g of 30% strength sodium methylate solution are added at room temperature. The reaction mixture warms to 30° C., whilst assuming an intense violet colour. The mixture is stirred at about 50° C. for 5 hours, thereafter diluted with 200 ml of methanol and adjusted to pH 7 with acetic acid. After the precipitate is filtered off, washed with methanol and dried, 39.4 g (85% of theory) of pale yellow crystals of the compound of the formula

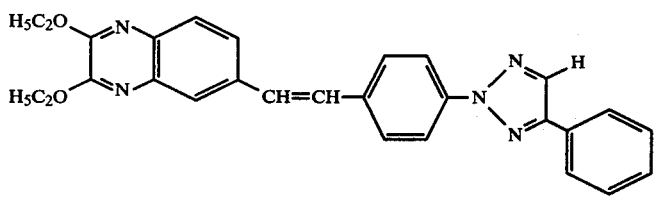
(26)

which is recrystallised from xylene/bleaching earth and, when dissolved in dimethylformamide, exhibits an intense blue fluorescence, are obtained.

The aldehyde of the formula

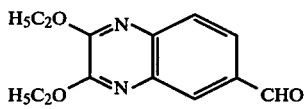
(27)

used is synthesised as follows:

31.1 g (0.1 mol) of crude 2,3-diethoxy-6-bromomethylquinoxaline are boiled under reflux with 15.5 g (0.11 mol) of hexamethylenetetramine in 100 ml of chloroform for 4 hours. Thereafter, 50 ml of chloroform are distilled off, the mixture is cooled and 50 ml of acetone are added. After filtering off the precipitate, 40.2 g of the urotropin salt are obtained, and are heated under reflux in 100 ml of 50% strength acetic acid for 2 hours. The solution is adjusted to pH 3 with about 10 to 20 ml of concentrated hydrochloric acid and, after being briefly boiled up, is cooled to 0° C. and 500 ml of water are added. The precipitate which has separated out is filtered off, washed with water until neutral and dried. 16 g (73.3% of theory) of colourless crystals which melt at 163° C. after recrystallisation from methylglycol are obtained.

The aldehyde of the formula

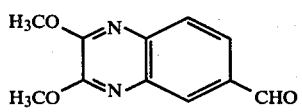
(28)

with the melting point 186° C. is also prepared analogously, in 65% yield.

EXAMPLE 8

Analogously to Example 7, the aldehyde (28) and the corresponding phosphonate give the compound of the formula

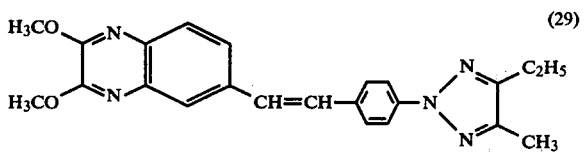
(29)

as yellow crystals which are recrystallised from xylene and exhibit greenish-tinged blue fluorescence in dimethylformamide.

Analogously to Examples 6 and 7, the derivatives of the general formula

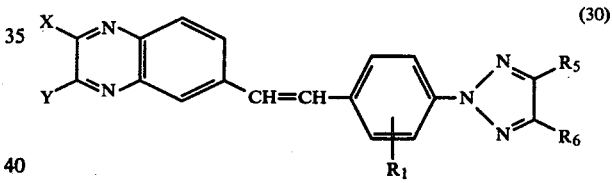
(30)

which are listed in Table II which follows are formed when the corresponding aldehydes are used.

Table II

| Compound | X | Y | $R_1$ | $R_5$ | $R_6$ | Fluorescence in dimethylformamide |
|---|---|---|---|---|---|---|
| 31 | Butoxy | Butoxy | H | Methyl | H | reddish-tinged blue |
| 32 | Chloro | Dimethylamino | 2-Chloro | Methyl | Methyl | blue |
| 33 | Morpholino | Morpholino | H | Ethyl | Methyl | blue-violet |
| 34 | Anilino | Ethoxy | H | Methyl | Phenyl | reddish-tinged blue |
| 35 | Piperidino | Methoxy | 2-Cyano | H | Phenyl | blue |
| 36 | Anilino | Anilino | H | Phenyl | Pheyl | violet |
| 37 | n-Propoxy | Ethylamino | 2-Carboethoxy | H | Styryl | red-violet |
| 38 | 2-Hydroxyethylamino | Butoxy | H | Phenyl | Chloro | reddish-tinged blue |
| 39 | Methylamino | Methoxy | H | Phenyl | Ethoxycarbonyl | blue |
| 40 | Benzylamino | Benzylamino | H | Phenyl | Cyano | deep blue |

EXAMPLE 9

Analogously to Example 7, 2,3-dimethoxy-6-formylquinoxaline and 5,6-dimethoxy-2-(4-diethoxyphosphonomethylphenyl)-2H-benzotriazole give the compound of the formula

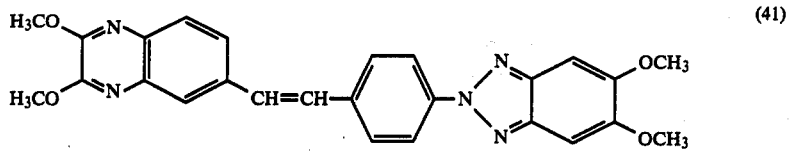

(41)

as pale yellow crystals which exhibit blue fluorescence in dimethylformamide.

EXAMPLE 10

In an analogous manner, the compound of the formula

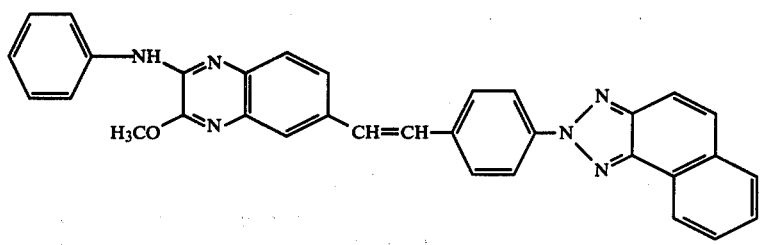

(42)

is obtained in the form of light yellow crystals which, when dissolved in dimethylformamide, exhibit reddish-blue fluorescence.

The 2H-Benzotriazole derivatives of the general formula

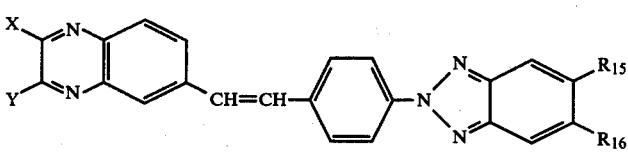

(43)

which are listed in Table III are obtained analogously.

3 hours. Thereafter, the mixture is cooled, discharged onto 500 ml of water and adjusted to pH 2 to 3 with concentrated hydrochloric acid. After the precipitate is filtered off, washed with water and dried, 28.5 g (85% of theory) of light yellow crystals of the formula

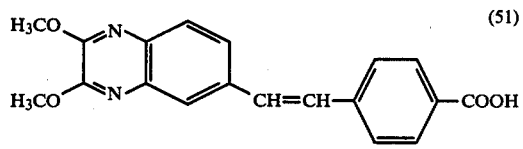

(51)

Table III

| Compound | X | Y | $R_{15}$ | $R_{16}$ | Fluorescence in dimethylformamide |
|---|---|---|---|---|---|
| 44 | Diethylamino | Chloro | Methyl | H | greenish-tinged blue |
| 45 | Methoxyethoxy | Methoxyethoxy | Methoxy | H | blue |
| 46 | Diethylamino | Ethoxy | Methoxy | Methoxy | blue |
| 47 | Piperidino | Piperidino | Bromo | Methoxy | blue |
| 48 | Benzoxy | Benzoxy | Methyl | Methoxy | greenish-tinged blue |
| 49 | Butoxy | Anilino | tert.-Butyl | H | greenish-tinged blue |
| 50 | Methoxy | Methoxy | H | H | blue-violet |

EXAMPLE 11

31.2 g (0.11 mol) of 2,3-dimethoxy-6-bromomethyl-quinoxaline, 56 g of triethyl phosphite and 100 ml of dimethylformamide are stirred at 120° to 150° C. for 4 hours. Thereafter, the excess triethyl phosphite and most of the dimethylformamide are distilled off in vacuo. The residue and 15 g (0.1 mol) of 4-formylbenzoic acid are suspended in 200 ml of dimethylformamide. 36 g of 30% strength sodium methylate solution are added dropwise to this suspension in the course of 20 minutes and the reaction mixture is stirred at 50° C. for which are purified by recrystallisation from dimethylformamide, are obtained.

33.6 g (0.1 mol) of the crude product corresponding to the compound (51) described above are converted into the acid chloride using 30 g of thionyl chloride and 2 g of dimethylformamide in 150 ml of xylene. 15 g (0.11 mol) of benzoic acid hydrazide are then introduced in portions. After the reaction has subsided the mixture is brought slowly to the reflux temperature and boiled for 3 hours. It is then cooled and distilled with steam. 35.2 g (81% of theory) of the compound of the formula

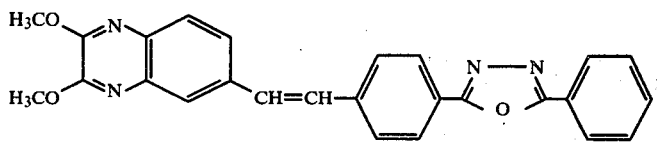

(52)

which exhibits red-violet fluorescence in dimethylformamide, are thus obtained.

EXAMPLE 12

According to Example 1, 5-biphenylyl-2-(4-formylphenyl)-1,3,4-oxidiazole and 2,3-dibutoxy-6-diethoxyphosphonomethylquinoxaline give the compound of the formula

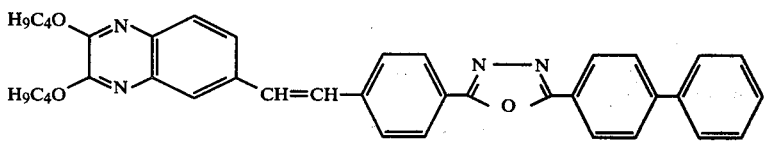

(53)

in 80% yield in the form of light yellow crystals, which are recrystallised from xylene and exhibit reddish-tinged blue fluorescence in dimethylformamide.

The oxidazole derivatives of the general formula

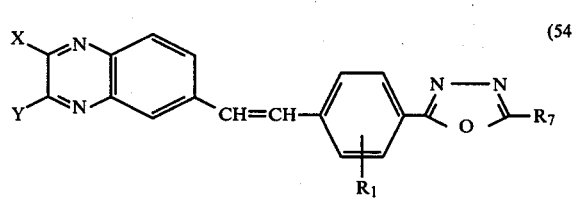

(54)

which are listed in Table IV which follows are likewise prepared.

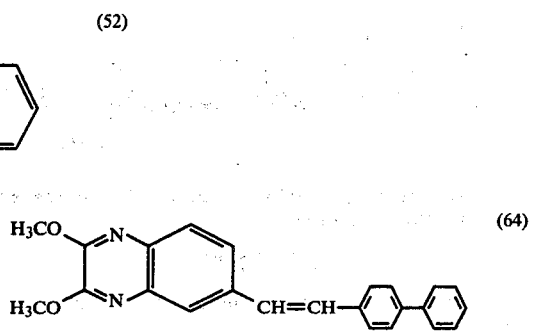

(64)

which is purified by recrystallisation from xylene, with the aid of bleaching earth, and, when dissolved in dimethylformamide, exhibits reddish-tinged blue fluorescence, are obtained.

EXAMPLE 14

Analogously to Example 11, 2,3-diethoxy-6-formylquinoxaline and 2-methoxy-4-formylbenzoic acid give the compound of the formula

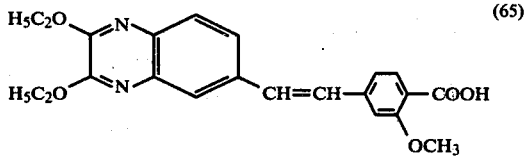

(65)

as pale yellow crystals which exhibit reddish-tinged blue fluorescence in dimethylformamide.

The compounds of the general formula

Table IV

| Compound | X | Y | $R_1$ | $R_7$ | Fluorescence in dimethylformamide |
|---|---|---|---|---|---|
| 55 | Ethoxy | Ethoxy | Cyano | Phenyl | blue |
| 56 | Anilino | Anilino | H | 4-Chlorophenyl | blue-violet |
| 57 | N-Morpholino | Methoxy | H | 4-Ethoxycarbonylphenyl | reddish-tinged blue |
| 58 | Methylamino | Methoxy | Ethoxycarbonyl | 4-Biphenylyl | blue |
| 59 | Benzylamino | Ethoxy | H | Styryl | red-violet |
| 60 | Ethoxy | Dimethylamino | H | 4-Carboxyphenyl | reddish-tinged blue |
| 61 | Methoxyethoxy | Methoxyethoxy | H | 2,4-Dichlorophenyl | reddish-tinged blue |
| 62 | Butoxy | Ethylamino | H | 4-Methoxyphenyl | reddish-tinged blue |
| 63 | Benzoxy | Benzoxy | H | 4-tert.-Butylphenyl | |

EXAMPLE 13

36 g of 30% strength sodium methylate solution are added dropwise to a solution of 31.2 g (0.1 mol) of 2,3-dimethoxy-6-dimethoxyphosphonomethylquinoxaline and 18.2 g (0.1 mol) of 4-formylbiphenyl in 200 ml of dimethylformamide in the course of 20 minutes and the mixture is stirred at 50° C. for 5 hours. It is then diluted with 100 ml of methanol and the pH is adjusted to 4 to 5 with acetic acid. After cooling to 0° C. and filtering off and drying the precipitate, 25.8 g (70% of theory) of crude product of the formula

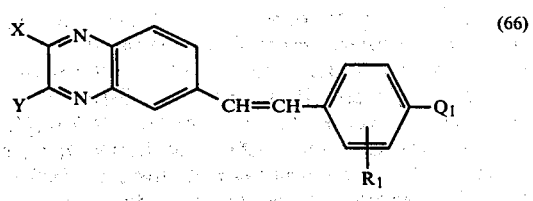

(66)

which are listed in Table V, can be prepared likewise.

Table V

| Compound | X | Y | $R_1$ | $Q_1$ | Fluorescence in dimethylformamide |
|---|---|---|---|---|---|
| 67 | Methoxy | Methoxy | 3-Cyano | Cyano | blue |
| 68 | Methoxy | Morpholino | 2-Cyano | Carboethoxy | red-violet |
| 69 | Dimethylamino | Ethoxy | 2-Chloro | Carbomethoxy | blue |
| 70 | 2-Hydroxyethylamino | 2-Hydroxyethylamino | 2-Methoxy | Cyano | reddish-tinged blue |
| 71 | Methoxyethoxyethoxy | Methoxyethoxyethoxy | 3-Chloro | Anilino-carbonyl | blue |
| 72 | Butoxy | Butoxy | H | 4-Methoxy-styryl | red-violet |

We claim:
1. Fluorescent dyestuff having the formula

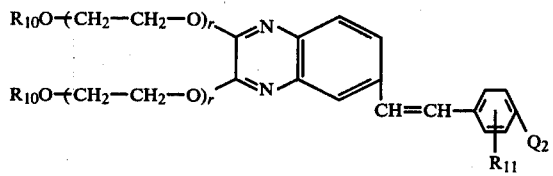

wherein
$R_{10}$ denotes $C_1$-$C_4$-alkyl,
$R_{11}$ denotes hydrogen or cyano,
r denotes an integer from 0 to 2,
$Q_2$ denotes a radical of the formulae

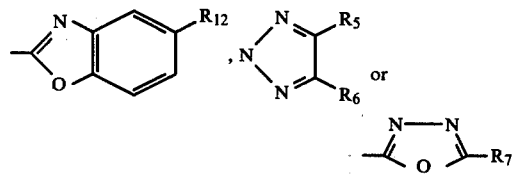

$R_{12}$ denotes hydrogen, chlorine, $C_1$-$C_4$-alkyl, phenyl-$C_1$-$C_3$-alkyl, cyclohexyl, phenyl, $C_1$-$C_4$-alkoxy, $C_1$-$C_4$-alkylsulphonyl, $C_1$-$C_4$-alkoxycarbonyl, cyano or carboxyl,
$R_5$ denotes $C_1$-$C_4$-alkyl, phenyl or styryl or, together with $R_6$, a fused-on benzo ring which is optionally substituted by $C_1$-$C_4$-alkyl, $C_1$-$C_4$-alkoxy or chlorine or fused-on naphtho,
$R_6$ denotes hydrogen, $C_1$-$C_4$-alkyl or phenyl or, together with $R_5$, a fused-on benzo ring which is optionally substituted by $C_1$-$C_4$-alkyl, $C_1$-$C_4$-alkoxy or chlorine or fused-on naphtho, and
$R_7$ denotes phenyl, styryl, biphenylyl or naphthyl, optionally substituted by $C_1$-$C_4$-alkyl, $C_1$-$C_4$-alkoxy, $C_1$-$C_4$-alkoxycarbonyl, cyano or chlorine.

2. Process for whitening synthetic, semi-synthetic or natural organic and high molecular weight materials with a whitening agent which said whitening agent is a fluorescent dye-stuff of the formula

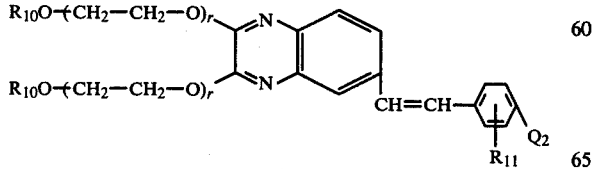

wherein
$R_{10}$ denotes $C_1$-$C_4$-alkyl,
$R_{11}$ denotes hydrogen or cyano,
r denotes an integer from 0 to 2,
$Q_2$ denotes a radical of the formulae

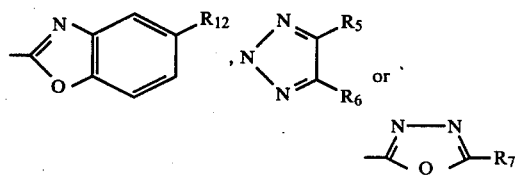

$R_{12}$ denotes hydrogen, chlorine, $C_1$-$C_4$-alkyl, phenyl-$C_1$-$C_3$-alkyl, cyclohexyl, phenyl, $C_1$-$C_4$-alkoxy, $C_1$-$C_4$-alkylsulphonyl, $C_1$-$C_4$-alkoxycarbonyl, cyano or carboxyl,
$R_5$ denotes $C_1$-$C_4$-alkyl, phenyl or styryl or, together with $R_6$, a fused-on benzo ring which is optionally substituted by $C_1$-$C_4$-alkyl, $C_1$-$C_4$-alkoxy or chlorine or fused-on naphtho,
$R_6$ denotes hydrogen, $C_1$-$C_4$-alkyl or phenyl or, together with $R_5$, a fused-on benzo ring which is optionally substituted by $C_1$-$C_4$-alkyl, $C_1$-$C_4$-alkoxy or chlorine or fused-on naphtho, and
$R_7$ denotes phenyl, styryl, biphenylyl or naphthyl, optionally substituted by $C_1$-$C_4$-alkyl, $C_1$-$C_4$-alkoxy, $C_1$-$C_4$-alkoxycarbonyl, cyano or chlorine.

3. Synthetic, semi-synthetic or natural organic high-molecular weight material whitened with a fluorescent dye-stuff of the formula

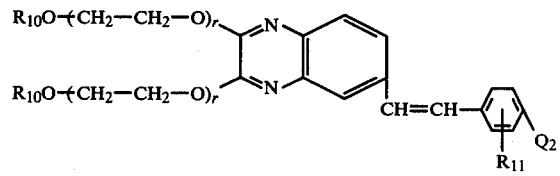

wherein
$R_{10}$ denotes $C_1$-$C_4$-alkyl,
$R_{11}$ denotes hydrogen or cyano,
r denotes an integer from 0 to 2,
$Q_2$ denotes a radical of the formulae

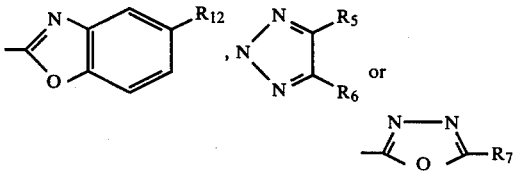

$R_{12}$ denotes hydrogen, chlorine, $C_1$-$C_4$-alkyl, phenyl-$C_1$-$C_3$-alkyl, cyclohexyl, phenyl, $C_1$-$C_4$-alkoxy, $C_1$–$C_4$-alkylsulphonyl, $C_1$–$C_4$-alkoxycarbonyl, cyano or carboxyl, $R_5$ denotes $C_1$–$C_4$-alkyl, phenyl or styryl or, together with $R_6$, a fused-on benzo ring which is optionally substituted by $C_1$–$C_4$-alkyl, $C_1$–$C_4$-alkoxy or chlorine or fused-on naphtho, $R_6$ denotes hydrogen, $C_1$–$C_4$-alkyl or phenyl or, together with $R_5$, a fused-on benzo ring which is optionally substituted by $C_1$–$C_4$-alkyl, $C_1$–$C_4$-alkoxy or chlorine or fused-on naphtho, and $R_7$ denotes phenyl, styryl, biphenylyl or naphthyl, optionally substituted by $C_1$–$C_4$-alkyl, $C_1$–$C_4$-alkoxy, $C_1$–$C_4$-alkoxycarbonyl, cyano or chlorine.

* * * * *